United States Patent
Odaibo

(10) Patent No.: US 12,424,300 B1
(45) Date of Patent: *Sep. 23, 2025

(54) CONDITIONAL MULTICAPITATE NEURAL NETWORKS FOR AI-BASED PROTEIN AND DRUG DESIGN

(71) Applicant: Stephen Gbejule Odaibo, Sugar Land, TX (US)

(72) Inventor: Stephen Gbejule Odaibo, Sugar Land, TX (US)

(73) Assignee: Deep EigenMatics LLC, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/178,769

(22) Filed: Apr. 14, 2025

(51) Int. Cl.
*G16B 15/30* (2019.01)
*G16B 15/20* (2019.01)
*G16B 40/20* (2019.01)

(52) U.S. Cl.
CPC ............ *G16B 15/30* (2019.02); *G16B 15/20* (2019.02); *G16B 40/20* (2019.02)

(58) Field of Classification Search
CPC ......... G16B 15/30; G16B 15/20; G16B 40/20
See application file for complete search history.

(56) References Cited

U.S. PATENT DOCUMENTS

| | | | |
|---|---|---|---|
| 11,923,044 B1 * | 3/2024 | Ford | G16B 15/20 |
| 12,243,292 B2 * | 3/2025 | Cheng | G06V 10/764 |
| 2022/0375538 A1 * | 11/2022 | Das | G06F 30/27 |
| 2024/0047006 A1 * | 2/2024 | Pan | G16B 15/30 |

FOREIGN PATENT DOCUMENTS

| | | | | |
|---|---|---|---|---|
| WO | WO-2024158987 A1 * | 8/2024 | | G16B 40/20 |
| WO | WO-2024262347 A1 * | 12/2024 | | G16C 20/30 |
| WO | WO-2025014634 A1 * | 1/2025 | | G16C 20/10 |

OTHER PUBLICATIONS

Sucholutsky, Ilia, et al. "Pay attention and you won't lose it: a deep learning approach to sequence imputation." PeerJ Computer Science 5 (2019): e210. (Year: 2019).*

(Continued)

*Primary Examiner* — Jesse P Frumkin

(57) ABSTRACT

Methods and apparatus for protein and drug design using multicapitate ("two or more headed") neural networks, wherein one head, a sequence head, is trained to generate the sequence of a protein, and another head, a structure head, is trained to generate the structure of the protein; and wherein the neural network is configured to accept a representation of a specified condition as input, and output a representation of a protein's sequence and structure. The structure head and sequence head each have their own loss functions, and the weights of the neural network body are shared, and jointly updated during training. Non-limiting examples of specified input conditions include representations of associated proteins and/or sets of properties of the desired output protein. Some embodiments of the invention include for the design and synthesis of effective peptide drug ligands, synthetic biologic antibody drugs, antibody drug conjugates, and monoclonal antibody (mAb) drugs.

13 Claims, 8 Drawing Sheets

Illustrative Example of a Backpropagation of Errors through a Bicapitate ("Two headed") Neural Network with a Sequence Head and a Structure Head.

(56) References Cited

OTHER PUBLICATIONS

Zhu, Baozhong, et al. "Improving drug-target interaction prediction through dual-modality fusion with InteractNet." Journal of bioinformatics and computational biology 22.5 (2024): 2450024. (Year: 2024).*

Andreeva, Antonina, et al. "SCOP database in 2004: refinements integrate structure and sequence family data." Nucleic acids research 32.suppl_1 (2004): D226-D229. (Year: 2004).*

Martinkus, Karolis, et al. "Abdiffuser: full-atom generation of in-vitro functioning antibodies." Advances in Neural Information Processing Systems 36 (2023): 40729-40759. (Year: 2023).*

Ruffolo, Jeffrey A., Jeffrey J. Gray, and Jeremias Sulam. "Deciphering antibody affinity maturation with language models and weakly supervised learning." arXiv preprint arXiv:2112.07782 (2021). (Year: 2021).*

* cited by examiner

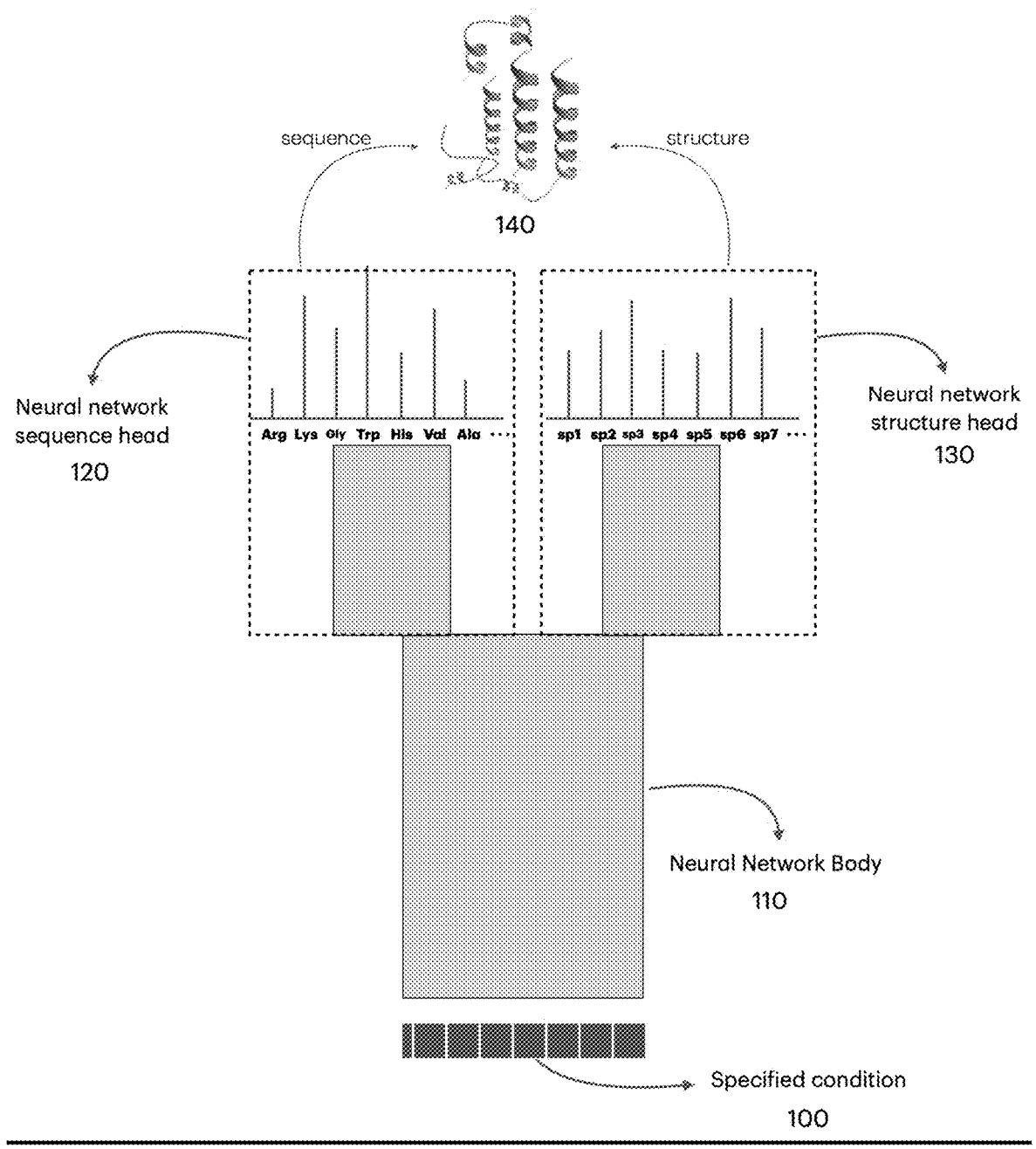
FIG. 1 Illustration of a Bicapitate ("Two headed") Neural Network with a Sequence Head and a Structure Head.

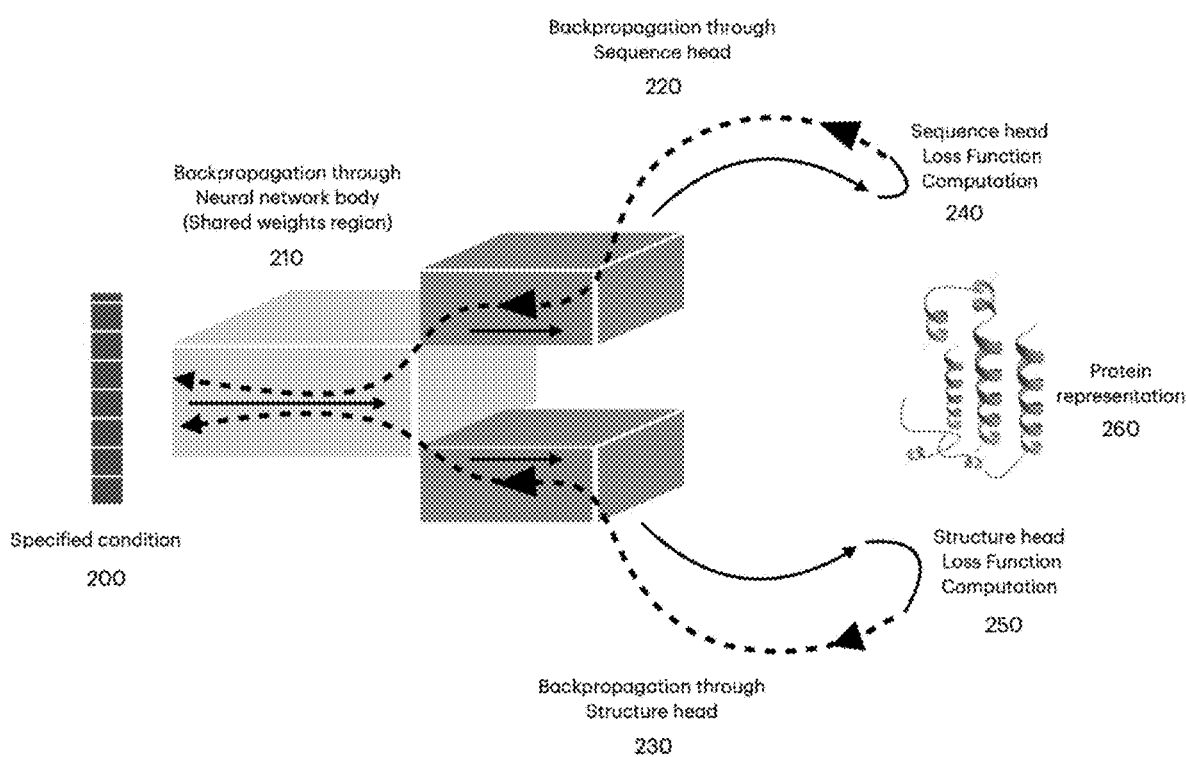
FIG. 2 Illustrative Example of a Backpropagation of Errors through a Bicapitate ("Two headed") Neural Network with a Sequence Head and a Structure Head.

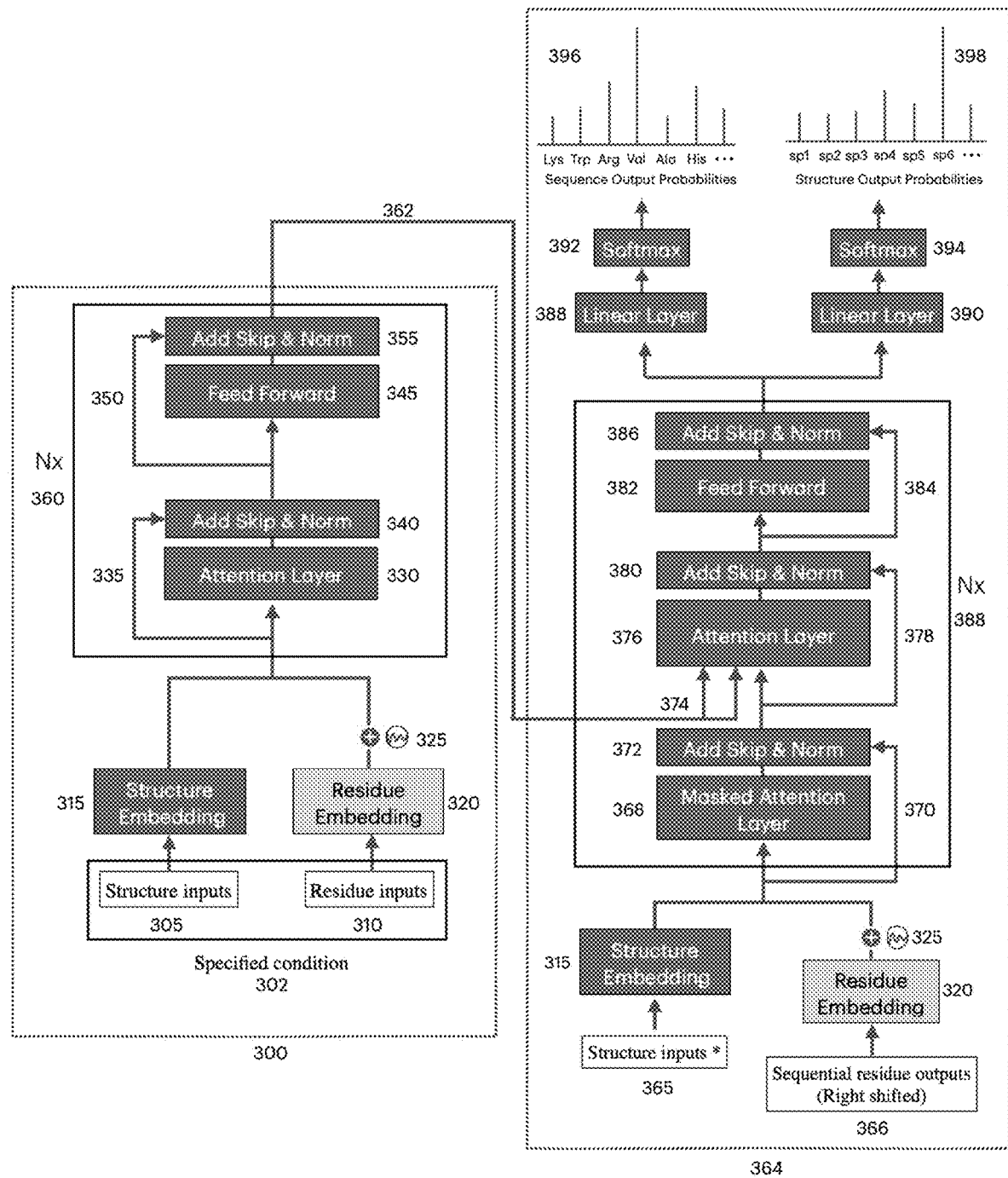
FIG. 3 Illustrative Example of a Training Architecture of a Bicapitate ("Two headed") Transformer Neural Network with a Sequence Head and a Structure Head.

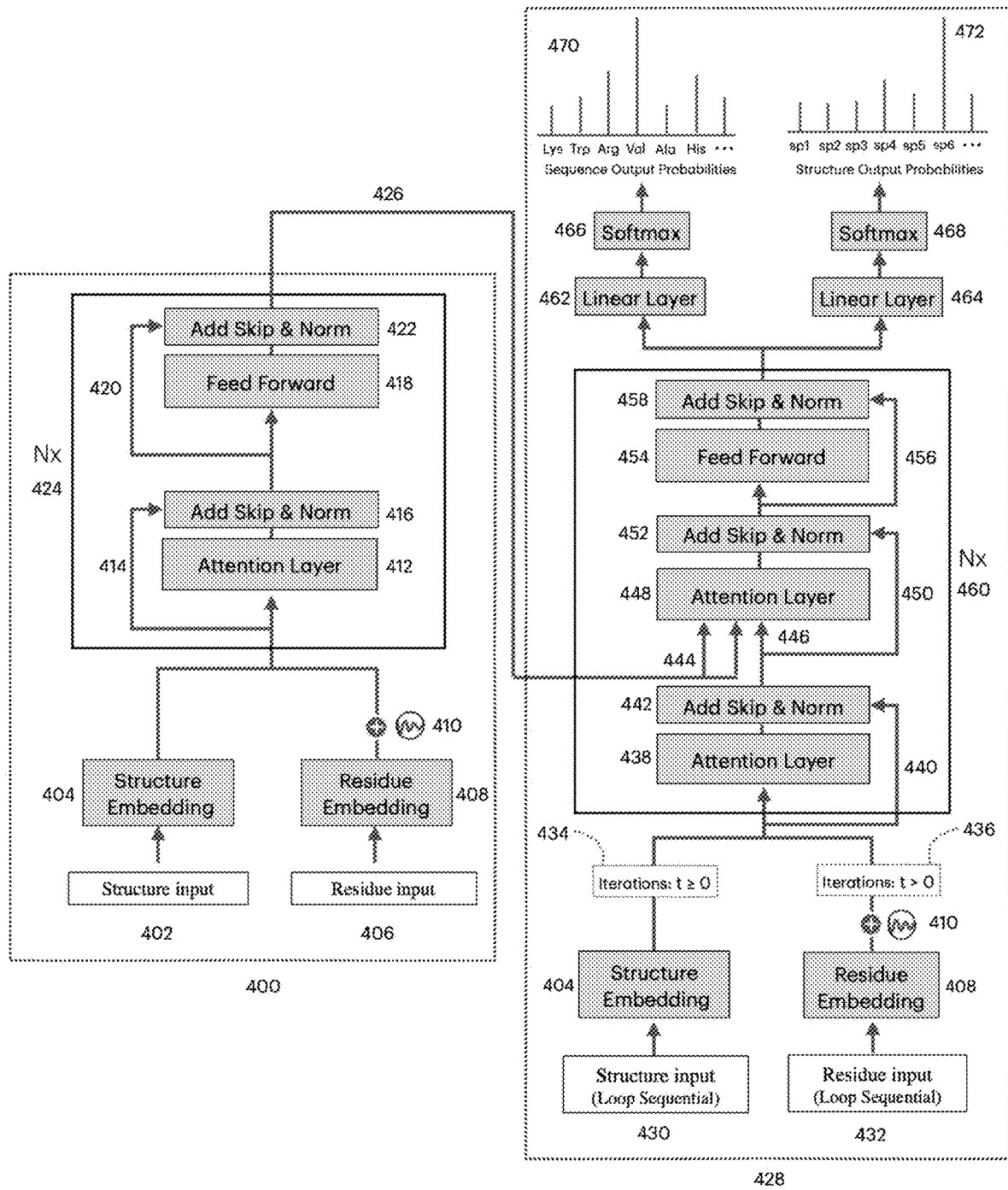
FIG. 4 Illustrative Example of an Inference Architecture of a Bicapitate ("Two headed") Transformer Neural Network with a Sequence Head and a Structure Head.

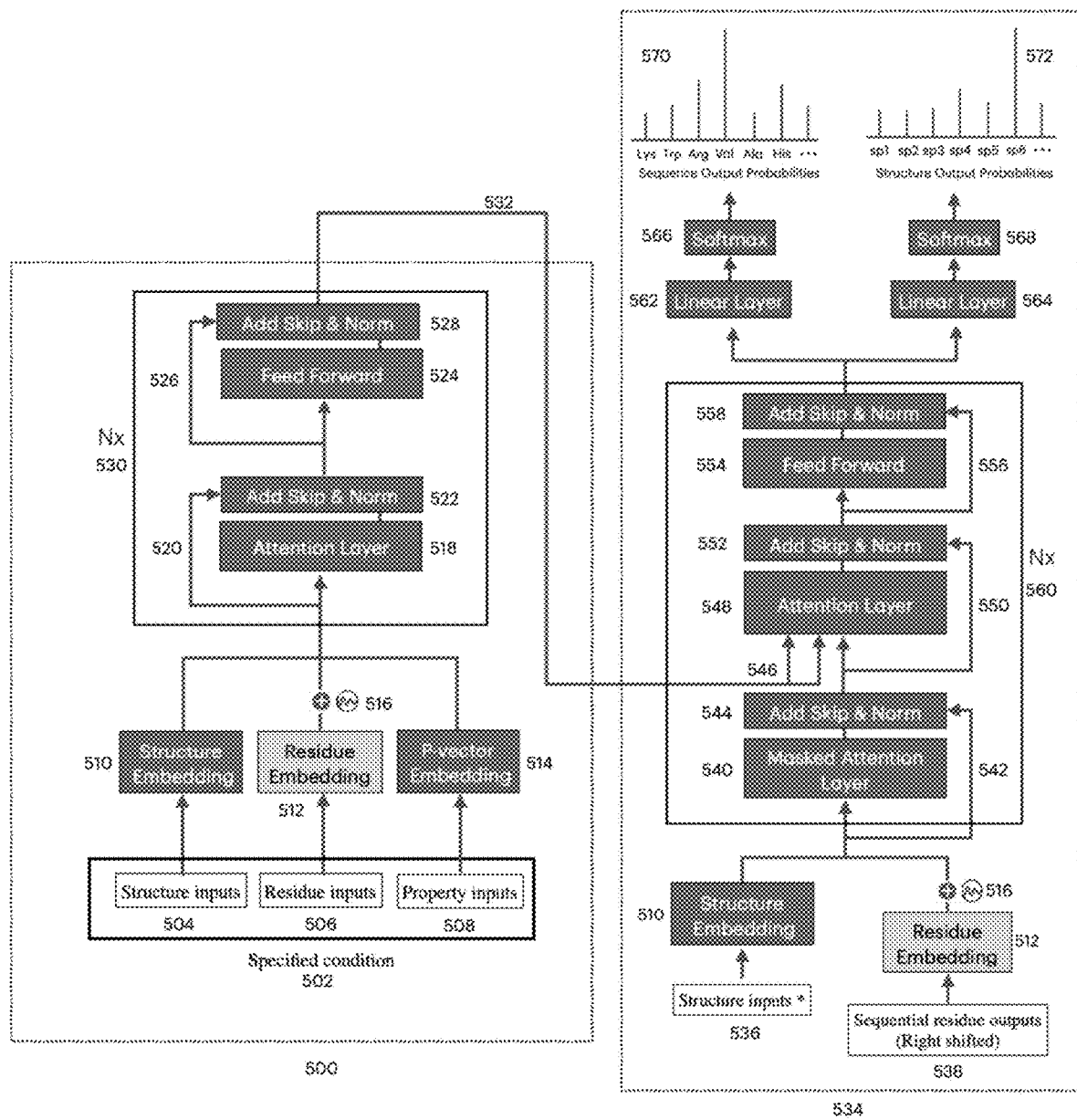
FIG. 5 Illustrative Example of a Training Architecture of a Bicapitate ("Two headed") Transformer Neural Network including a P-vector Embedding Specified Condition.

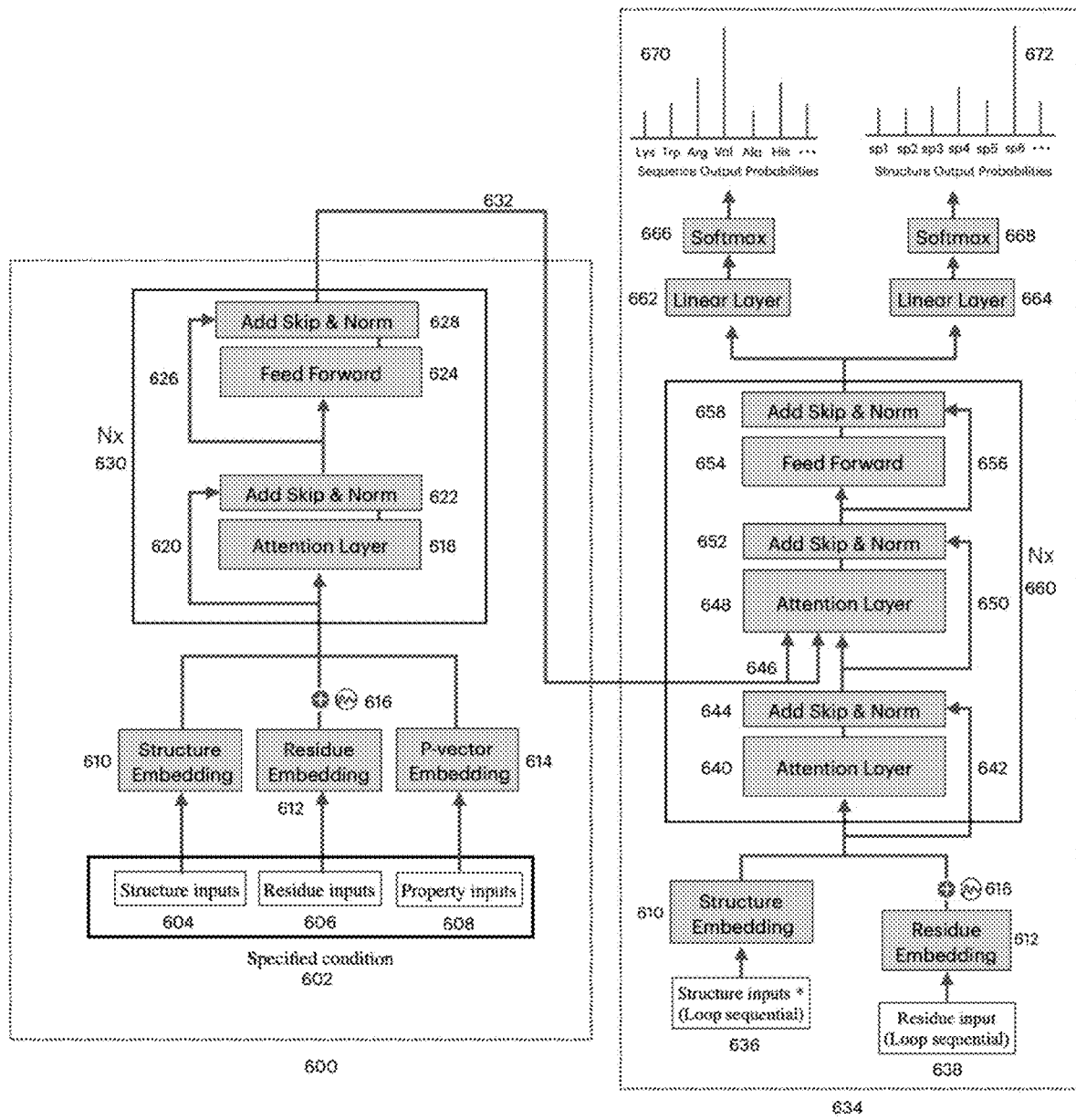
FIG. 6 Illustrative Example of an Inference Architecture of a Bicapitate ("Two headed") Transformer Neural Network including a P-vector Embedding Specified Condition.

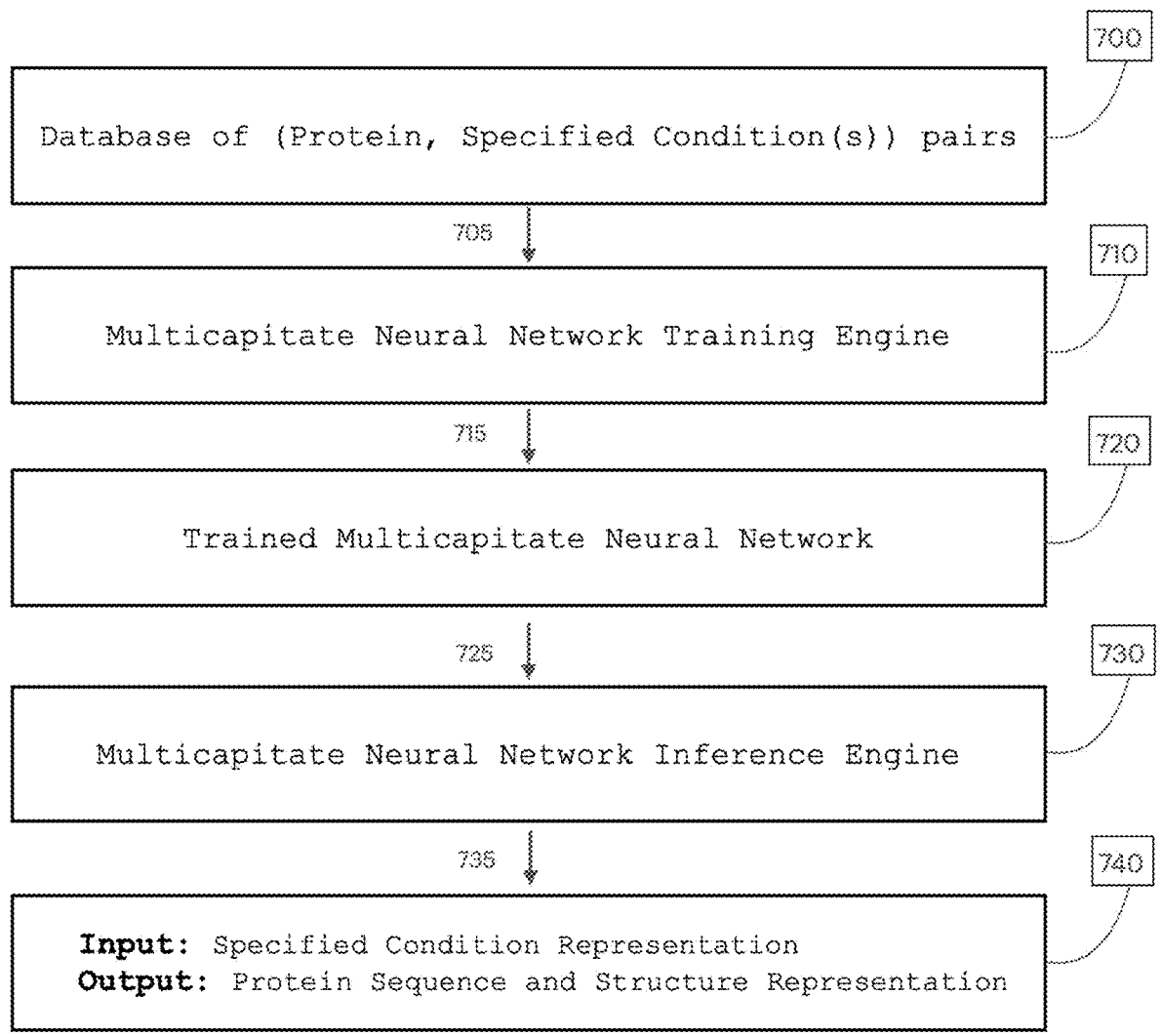
FIG. 7 Schematic Flow Diagram of Multicapitate Neural Network Inference

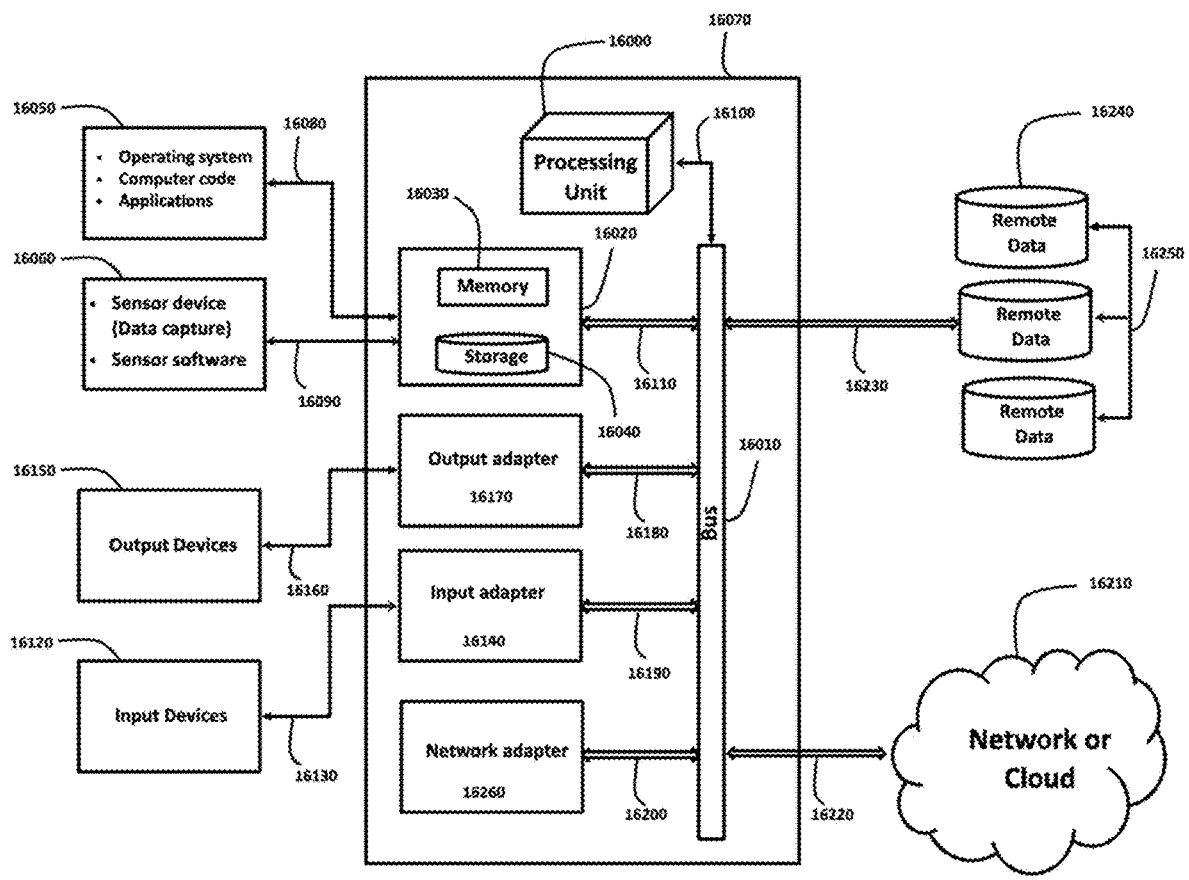
FIG. 8 Computing Environment

CONDITIONAL MULTICAPITATE NEURAL NETWORKS FOR AI-BASED PROTEIN AND DRUG DESIGN

FIELD OF THE INVENTION

The present invention relates generally to Artificial Intelligence (AI) and Machine Learning (ML) methods for protein and drug ligand design, and specifically to use of neural networks for determining sequence and structure representations of proteins, given specified conditions.

BACKGROUND OF THE INVENTION

Proteins are defined by their sequence and structure, and they mediate essentially all cellular processes. Therefore most diseases result from protein dysfunction or deficiency; and as such, a fully integrated approach to determining sequence and structure holds great potential to enhance the drug discovery and development process.

Currently, the research and development pipeline for new drugs is tremendously expensive and lengthy, often costing over $2 billion and more than 10 years to get a single candidate drug through clinical testing phases. Yet despite the exorbitant investment of time and resources, a high percentage of drugs fail in the clinical testing phases.

Deep learning methods are increasingly being applied towards solving problems in protein and drug design. Nonetheless, there remains significant gaps and a conspicuously unmet need for deep learning methods that learn sequence and structure of proteins and drug ligands in a fully integrated way.

Most of the existing deep learning methods for protein and drug design do not address sequence and structure in a fully integrated manner. Instead, sequence and structure are often treated separately. For instance, one method is typically used to determine sequence, and then given that sequence, a structure is then inferred using another method or network. This is often called the "protein folding problem." In certain instances, such an approach may be appropriate, however, it fails to generalize to many use cases such as the design of novel and effective drugs. This lack of network integration likely contributes significantly to the high failure rate of new drugs in clinical trials.

On the one hand, if an endogenous protein is sequenced, then separately determining its structure may suffice. However, in the case of designing drug ligands for known targets, the search space is exponentially large and requires more clever and integrated approaches. In particular, given a specified condition on a protein whose sequence and structure one seeks to obtain using deep learning methods, it is critical to determine the sequence and structure in a unified and fully integrated manner. This can be accomplished by having a neural network wherein the architecture and training procedure guarantees joint learning of sequence and structure.

In this disclosure, we present such an invention: a multicapitate ("two or more heads") neural network with a sequence head which generates the sequence and a structure head which generates the structure, given as input, a specified condition on the desired output protein. Importantly, the weights in the body (i.e. the non-capitate weights) of the neural network are shared between the heads in the sense that during training, backpropagation and weight updates proceed backwards independently from each of the heads through all ancestral nodes of the respective head.

Prior to this disclosure, there were no neural networks with two or more heads that included a sequence head and a structure head for jointly learning the sequence and structure respectively of a protein, given a specified condition. This unmet need is significant. This invention addresses that need and therefore provides a method with an increased likelihood of yielding novel effective drugs to treat disease.

OBJECTS OF THE INVENTION

It is an object of this invention to provide a system, method, and apparatus for obtaining a sequence and structure representation of a protein for synthesis, given as input, a representation of a specified condition on that protein.

Another object of this invention is to provide a system, method, and apparatus for obtaining a jointly learned representation of sequence and structure of a protein for synthesis, given as input, a representation of a specified condition on that protein.

Yet other objects, advantages, and applications of the invention will be apparent from the specifications and drawings included herein.

SUMMARY OF THE INVENTION

The invention disclosed herein includes a method for obtaining a jointly learned representation of sequence and structure of a protein for synthesis, given as input, a representation of a specified condition on that protein. The method comprises receiving at a processor, representations of a plurality of proteins; wherein for each of the plurality of proteins, the representations include a sequence and structure representation as well as a representation of specified condition(s) on the protein. The representations of the plurality of proteins are used to train a multicapitate neural network consisting of at least two heads, a sequence head which generates the sequence and a structure head which generates the structure.

Furthermore, the multicapitate neural network is configured to accept as input, a representation of the specified condition, and to yield as output, a sequence and structure representation of the protein. The weights in the neural network body (i.e. non-capitate weights) are shared between the neural network heads. For instance, in one embodiment of the invention wherein training is via gradient descent, during the training process, backpropagation and weight updates proceed backwards from each head through all ancestral nodes of that head.

In the context of supervised learning, the representation of the specified conditions on the protein is the "input data", while the sequence and structure representation of the protein is the "label." Furthermore, in some embodiments, the specified condition includes a sequence and structure representation of an associated protein ("target protein"). For example, the associated protein may be a target receptor, and the desired output protein a ligand of that receptor. The condition may be further specified using a property vector (p-vector), which encodes desired properties on the output protein. In the example of a ligand, the p-vector may numerically encode properties such as agonism class, peptide size, amino acid composition, etc.

In some embodiments, the base structure of the neural network is a transformer. There are a wide diversity of architectural schemes such as encoder-decoder, encoder-only, decoder-only, and various hybrid implementations of transformers that can be used or devised. There are also a wide diversity of means for encoding the specified condition as well as for entering it as input into the neural network. A few non-limiting examples include inputting the specified condition into the encoder side of an encoder-decoder architecture and connecting the encoder output to a cross-attention layer. The input may be standardized and embedded using embedding neural network matrices with learnable weights.

Some non-limiting applications of embodiments of the invention include for the design and synthesis of effective peptide drug ligands, synthetic biologic antibody drugs, antibody drug conjugates, and monoclonal antibody (mAb) drugs.

In summary, the invention disclosed herein includes methods using a multicapitate neural network for obtaining a jointly learned sequence and structure representation of a protein for synthesis, given as input, a representation of a specified condition on that protein.

The invention consists of several outlined processes below, and their relation to each other, as well as all modifications which leave the spirit of the invention invariant. The scope of the invention is outlined in the claims section.

BRIEF DESCRIPTION OF THE DRAWINGS

In the following detailed description of the invention, we reference the herein listed drawings and their associated descriptions, in which:

FIG. 1 is an illustration of a bicapitate ("two headed") neural network with a sequence head and a structure head.

FIG. 2 is an illustrative example of a backpropagation of errors through a bicapitate neural network with a sequence head and a structure head.

FIG. 3 is an illustrative example of a training architecture of a bicapitate transformer neural network with a sequence head and a structure head.

FIG. 4 is an illustrative example of an inference architecture of a bicapitate transformer neural network with a sequence head and a structure head.

FIG. 5 is an illustrative example of a training architecture of a bicapitate transformer neural network including a p-vector embedding specified condition.

FIG. 6 is an illustrative example of an inference architecture of a bicapitate transformer neural network including a p-vector embedding specified condition.

FIG. 7 is a schematic flow diagram of multicapitate neural network inference.

FIG. 8 is an example of a computing environment.

DETAILED DESCRIPTION OF THE PREFERRED EMBODIMENTS

The illustration in FIG. 1 is of a bicapitate ("two headed") neural network with a sequence head 120 and a structure head 130. The neural network is configured to accept a representation of a specified condition 100 as input. The weights in the neural network body 110 are shared between the two heads, while the weights within each of the heads are not directly shared. In the illustrated embodiment, residue-wise, the final output layer of each of the heads yields a probability distribution over possible outputs. For the sequence head, the distribution is over the amino acids and auxiliary tokens such as <end-of-peptide> representation. For the structure head, the distribution is over the set of possible structure parameters for a residue. Together, the output of the sequence head and the structure head yield the representation of the output protein 140.

As noted, the weights in the body of the bicapitate neural network of FIG. 1 are shared. The mechanism of the weight sharing is further illustrated in FIG. 2. In particular, consider an embodiment that utilizes gradient descent to train the bicapitate neural network. During the forward pass, the representation of the specified condition 200 is acted on and transformed by the successive layers of the neural network body. The final output layer of the neural network body leads to each of the respective heads. Each of the heads terminates in a final output layer at which that head's loss function value is computed during training. In the case of the sequence head, the loss function computation 240 provides the errors which are then backpropagated 220 through all network nodes that contributed to the sequence head loss function value. The backpropagation and corresponding weight updates proceed backwards through the sequence head and onwards through the entirety of the neural network body 210.

Similarly, for the structure head. During training, the forward pass proceeds through the neural network body and into the structure head, terminating in the structure head's loss function computation 250. This provides the structure losses which are then backpropagated 230 from the structure head terminus, through the structure head, and then through the body 210, updating all encountered weights along the way.

The training data consists of representations of a plurality of proteins 260, wherein the representations of each of the plurality of proteins includes a sequence and structure representation. In addition to the sequence and structure representation, the representations of each of the plurality of proteins also includes a representation of a specified condition (or set of conditions) 200. In a standard supervised learning sense, the specified condition representation is the data and the sequence and structure representation is the data label. The supervised learning training objective is therefore to train the neural network to be able to generate a protein's sequence and structure representation, given a specified condition representation.

FIG. 3 is an illustrative example of a training architecture of a bicapitate transformer neural network with a sequence head and a structure head. The neural network training objective in this embodiment is: given a sequence and structure representation of a protein (the specified condition or "data") in association with a desired output protein, learn to generate the sequence and structure representation of the desired output protein ("the label"). In the embodiment of the invention exemplified in FIG. 3, the transformer architecture is encoder-decoder with the encoder 300 accepting a sequence representation 310 and a structure representation 305 of the associated protein, together constituting the specified condition 302. The decoder 364 accepts input both directly as well as from the encoder. The final output layer context array of the encoder enters the decoder for cross-attention 374. Additionally, in this embodiment, the decoder contains a residue-wise autoregression of the transformer. The transformer in this exemplified embodiment is bicapitate (has two heads), a sequence head which generates an residue output probability 396 and a structure head which generates structure output probabilities 398.

As noted, the embodiment illustrated in FIG. 3 is for training, wherein the training objective is for the trained transformer to generate a representation of peptide sequence and structure, given a sequence and structure representation of an associated protein. An example of an associated protein-output protein pair is a target receptor (associated protein) and a peptide ligand (output protein). For a more general extension of this particular non-limiting example, in any protein-protein complex, one constituent protein can be designated and treated as the output protein, while the remaining protein or subcomplex can be designated and treated as the target (the specified condition).

The encoder 300 accepts a structure input vector 305 into the structure embedding 315. The structure input vector is a vector of structure parameters. In one embodiment, it is of fixed length, L, and zero padding is used for target proteins whose structure parameters are represented by a vector of smaller length than the fixed length, L. The fixed length, L, is a hyperparameter.

The structure embedding is a weight matrix, $W_s$, which the structure input vector, x, 305 multiplies to yield the structure embedding vector, s, as follows:

$$W_s x = s$$

where $W_s$ is an m×L matrix, L is the fixed length of the structure input vector, and m is the length of the amino acid residue embedding vectors. Both m and L are hyperparameters of the model.

The target protein's amino acid residue inputs 310 can be in the form of one-hot-encoder vectors which are passed into the residue embedding 320, wherein the residue embedding is itself a trained neural network. A position encoding 325 can be added to the output residue embedding vectors to imprint a signal of sequence position on the respective residue embeddings.

An array of vectors consisting of the structure embedding vector(s) and each of the residue embedding vectors of the target protein is passed as input into an attention layer 330. There are a plurality of ways to implement attention mechanisms. In one embodiment, attention layers consist of three types of weight matrices: a query weight matrix, $W_q$, a key weight matrix, $W_k$, and a value weight matrix, $W_v$. Each of the embedding vectors in the array are then multiplied by each of the three matrices to obtain respective queries, keys, and values, as follows:

$$W_q u = q$$

$$W_k u = k$$

$$W_v u = v$$

where u is an embedding vector (i.e. either the structure embedding vector s or one of the residue embedding vectors r).

For each embedding vector in the array, its respective query vector is dotted with the key vectors of all token representations in the context array. Next, a softmax operation is done on the resulting array to yield a probability distribution for each token. Next, for each token, a linear combination of values v is taken wherein the coefficient of each value is the respective probability (i.e. attention weight). The output of this linear combination is then taken as the token's respective output into the next layer of the transformer. This is done for each token in the encoder, therefore the length of the input array and the length of the output array from this attention layer 330 are the same. Given the ith token, its corresponding coefficient associated with the jth token can be denoted $c_{ij}$ and is given by, $$c_{ij} = \frac{e^{<q_i, k_j>}}{\sum_p e^{<q_i, k_p>}}$$

The attention layer output of the ith token can be denoted $o_i$ and is then given by, $$o_i = \Sigma_j c_{ij} v_j$$

In some embodiments, the dot product $<q_i, k_j>$ can be scaled by a variance factor.

The array of outputs $o_i$ are then passed into a normalization layer 340. Furthermore, a copy of the input array which was passed into the attention layer is passed 335 into and added to a normalization layer, skipping the attention layer. This skip connection serves to preserve the pre-attention layer character signal thereby enhancing available signals for learning.

The output from the Add skip & Norm layer 340 is passed into a feed forward neural network layer 345 and from there into another Add skip & Norm layer 355. The block module 360 of "attention→add skip & norm→feed forward→Add-skip & norm" is repeated N number of times where N is a hyperparameter of the model architecture.

The final output array of the encoder part is then passed 362 into the decoder part 364. In particular, it enters the decoder at a cross attention layer 374, wherein the encoder output array joins the incoming token from the preceding layer 372 of the decoder. The subject token then attends to all elements in the combined array via the previously described attention mechanism, hence the term cross attention.

The decoder receives input both from the encoder via cross attention input 374 as well as directly via the structure vector input 365 (and autoregressively via residue inputs 366). Notably, in some embodiments, the structure outputs from the emerging output protein can also be served as inputs autoregressively (in addition to the target structure input). The structure vector input enters a self-attention layer 368 whose context array—in one embodiment of the invention—initially consists of only one token, the structure embedding vector, which self-attends to itself; after which it is passed to add skip & norm layer 372 and then onwards to cross attention layer 376. The block module 388 repeats N times where N is a hyperparameter of the model.

In other embodiments, the residue embeddings aspect of the target (specified condition) can also be incorporated into the direct input context array of the decoder, thereby serving not only in the cross-attention module but also in the self-attention module.

The transformer training architecture is designed for parallelism. In particular, for each amino acid residue token representation in an output protein sequence to be generated, the preceding amino acid residues of the output protein as well as the label (i.e. the correct amino acid residue token) are both known and available for end-to-end differentiable supervised learning. Hence the prediction of each amino acid residue token can be run simultaneously with the shared weights of the architecture being updated simultaneously. Here, by shared weights we mean all the weights of the transformer are shared between residue threads. This is different from the earlier described weight sharing in the network body by the respective heads.

The implementation of the weight sharing between residue threads is reflected in the causal masking of the residue-level masked attention layer 368, wherein for any given residue in the output protein representation, the preceding sequence and structure representations of the output protein are visible to the prediction algorithm and used in attention layer, but its residue answer label (i.e. identity and structure representation of the correct next amino acid in the sequence) is masked from the prediction algorithm.

End-to-end stochastic gradient descent (or other optimization), is then performed in parallel for each amino acid, wherein each parallel process updates the set of shared weights as it proceeds. This parallelism, however, is simply an implementation embodiment example, and not a limitation of the invention in any way.

In the embodiment of FIG. 3, the <start-of-sequence> token is taken as the structure input vector 365 of the target protein. Subsequent subject tokens are the leading amino acid residues and are passed in from the final output layer in an autoregressive manner. As noted however, since both the preceding residues of the output protein and the residue answer labels are fully known during training, the architecture is such that training can be done in parallel i.e. without needing to wait in sequence.

In another embodiment, the structure input vector 365 is updated with each iteration of the autoregression, as the residues of the emerging output protein become known, the length of the zero padding aspects of the fixed length structure input vector decreases by 1, and the learnable structure embedding is computed via matrix multiplication as described.

The sequence head's final layer output probabilities 396 are over representations of the amino acids and auxiliary tokens such as an <end-of-sequence> token. By way of example but not limitation, a cross-entropy loss function can be implemented and then stochastic gradient descent (or other optimization) used to optimize the model. Therefore, backpropagation of errors computed at the sequence head terminal results in weight updates in the sequence head as well in all other upstream weights in the transformer body that contributed to the sequence head loss. In this sense, the non-capitate weights are shared.

Similarly, the structure head's final layer output probabilities 398 are over the structure parameters for encoding a residue. By way of example but not limitation, they may be spatial coordinate locations of the voxels in a 3D grid, or they may be unique identifiers ("address") of the voxels in a 3D grid, or representative values of a discretization of the range of possible torsion angles. Similarly to the sequence head, by way of example but not limitation, a cross-entropy loss function can be implemented and then stochastic gradient descent (or other optimization) used to optimize the model. Therefore, backpropagation of errors computed at the structure head terminal results in weight updates in the structure head as well in all other upstream weights in the transformer body that contributed to the structure head loss. In this sense, the non-capitate weights are shared.

FIG. 4 is an illustrative example of an inference architecture for output protein determination using a trained bicapitate transformer. The objective of this exemplified embodiment of the invention is: given a sequence and structure representation of a target protein (specified condition), generate a sequence and structure representation for a desired output protein.

One set of differences between the training (FIG. 3) and the inference (FIG. 4) architectures of the bicapitate transformer stems from parallelizeability, in that the training architecture is parallelizeable while the inference architecture is not parallelizeable in the same way. In particular, in the training architecture, since the labels and inputs are all known during training, there is a need for masking in the decoder's attention layer 368. However, in the inference architecture, the residue generation must be done sequentially, hence no masking needed.

The other set of differences between the training (FIG. 3) and the inference (FIG. 4) architectures, stems from the basic purpose of training vs inference. In particular, since the inference architecture does not involve training, the sequence and structure heads are not associated with a loss function. Instead, they simply terminate with their respective output probabilities 470 and 472. The weights are learnable only during training (FIG. 3) but are frozen during inference (FIG. 4).

FIG. 5 is an illustrative example of a training architecture of a bicapitate transformer neural network including a p-vector embedding specified condition. The p-vector stands for "property vector" and is a specified condition of property inputs 508 encoded as a vector. The p-vector embedding 514 is a matrix whose entries are a subset of the learnable weights of the transformer. The p-vector can be organized in a plurality of ways to encode condition properties of the output protein. Each entry position of the p-vector can represent a different property which can be categorical or continuous. By way of example but not limitation, consider a scenario in which the target protein is a receptor, and the output protein is a ligand of that receptor; wherein the specified condition includes a specification of the target protein sequence and structure as well as a p-vector. The p-vector entries can be implemented to numerically encode desired properties of the ligand. By way of non-limiting example, the p-vector entries may include (i) agonism [agonist vs antagonist], (ii) peptide size in daltons range category, (iii) peptide length (number of amino acids) range category, (iv) amino acid composition category, and/or (v) secondary structure motif composition category.

In this embodiment, the p-vector embedding matrix 514 is of size m×P where P is the length of the p-vector and m is the length of the vector outputs of the residue embedding 512 and the structure embedding 510.

FIG. 6 is an illustrative example of an inference architecture of a bicapitate transformer neural network including a p-vector embedding specified condition 608. The differences from the training architecture stem from (i) no residue-wise parallelism in the inference architecture hence no causal masking, and (ii) no loss function computation and optimization in the inference case.

FIG. 7 is a schematic flow diagram of an embodiment of multicapitate neural network inference. A database 700 consisting of representations of a plurality of proteins is used to train a multicapitate neural network, consisting of a sequence head and a structure head each with its own loss function. For each of the plurality of proteins, the representations include a sequence and structure representation which serves as the "label" associated with that protein. The associated input data associated with that protein is the specified condition. As we saw in the previous non-limiting examples of FIGS. 3-6, the specified condition can itself include a sequence and structure representation of an associated protein ("target protein"). In addition, as we saw in the non-limiting example of FIG. 5-6, the specified condition can include desired properties on the output protein, and these can be encoded as a p-vector.

The representations of a plurality of proteins from the database 700 are passed into a multicapitate neural network training engine 710 to yield a trained multicapitate neural network 720. The trained multicapitate neural network is the primary component of the inference engine 730. The inference engine is configured and trained to take an instance of a specified condition representation as input, and yield a desired protein sequence and structure as output.

Ones with ordinary skill in the art will recognize that the invention disclosed herein can be implemented over an arbitrary range of computing configurations. We will refer to any instantiation of these computing configurations as the computing environment. An illustrative example of a computing environment is depicted in The Computing Environment FIG. Examples of computing environments include but are not limited to desktop computers, laptop computers, tablet personal computers, mainframes, mobile smart phones, smart television, programmable hand-held devices and consumer products, distributed computing infrastructures over a network, cloud computing environments, or any assembly of computing components such as memory and processing—for example.

As illustrated in The Computing Environment FIG, the invention disclosed herein can be implemented over a system that contains a device or unit for processing the instructions of the invention. This processing unit 16000 can be a single core central processing unit (CPU), multiple core CPU, graphics processing unit (GPU), multiplexed or multiply-connected GPU system, or any other homogeneous or heterogeneous distributed network of processors.

In some embodiment of the invention disclosed herein, the computing environment can contain a memory mechanism to store computer-readable media. By way of example and not limitation, this can include removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer.

As depicted in The Computing Environment FIG, the computing environment can include a system memory 16030 which can be volatile memory such as random access memory (RAM) and may also include non-volatile memory such as read-only memory (ROM). Additionally, there typically is some mass storage device 16040 associated with the computing environment, which can take the form of hard disc drive (HDD), solid state drive, or CD, CD-ROM, blu-ray disc or other optical media storage device. In some other embodiments of the invention the system can be connected to remote data 16240.

The computer readable content stored on the various memory devices can include an operating system, computer codes, and other applications 16050. By way of example not limitation, the operating system can be any number of proprietary software such as Microsoft windows, Android, Macintosh operating system, iphone operating system (iOS), or Linux commercial distributions. It can also be open source software such as Linux versions e.g. Ubuntu. In other embodiments of the invention, data processing software and connection instructions to a sensor device 16060 can also be stored on the memory mechanism. The procedural algorithm set forth in the disclosure herein can be stored on—but not limited to—any of the aforementioned memory mechanisms. In particular, computer readable instructions for training and subsequent image classification tasks can be stored on the memory mechanism.

The computing environment typically includes a system bus 16010 through which the various computing components are connected and communicate with each other. The system bus 16010 can consist of a memory bus, an address bus, and a control bus. Furthermore, it can be implemented via a number of architectures including but not limited to Industry Standard Architecture (ISA) bus, Extended ISA (EISA) bus, Universal Serial Bus (USB), microchannel bus, peripheral component interconnect (PCI) bus, PCI-Express bus, Video Electronics Standard Association (VESA) local bus, Small Computer System Interface (SCSI) bus, and Accelerated Graphics Port (AGP) bus. The bus system can take the form of wired or wireless channels, and all components of the computer can be located remote from each other and connected via the bus system. By way of example and not of limitation, the processing unit 16000, memory 16020, input devices 16120, output devices 16150 can all be connected via the bus system. In the representation depicted in The Computing Environment FIG, by way of example not limitation, the processing unit 16000 can be connected to the main system bus 16010 via a bus route connection 16100; the memory 16020 can be connected via a bus route 16110; the output adapter 16170 can be connected via a bus route 16180; the input adapter 16140 can be connected via a bus route 16190; the network adapter 16260 can be connected via a bus route 16200; the remote data store 16240 can be connected via a bus route 16230; and the cloud infrastructure can be connected to the main system bus vis a bus route 16220.

In some embodiment of the invention disclosed herein, The Computing Environment FIG illustrates that instructions and commands can be input by the user using any number of input devices 16120. The input device 16120 can be connected to an input adapter 16140 via an interface 16130 and/or via coupling to a tributary of the bus system 16010. Examples of input devices 16120 include but are by no means limited to keyboards, mouse devices, stylus pens, touchscreen mechanisms and other tactile systems, microphones, joysticks, infrared (IR) remote control systems, optical perception systems, body suits and other motion detectors. In addition to the bus system 16010, examples of interfaces through which the input device 16120 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein, The Computing Environment FIG illustrates that output data, instructions, and other media can be output via any number of output devices 16150. The output device 16150 can be connected to an output adapter 16170 via an interface 16160 and/or via coupling to a tributary of the bus system 16010. Examples of output devices 16150 include but are by no means limited to computer monitors, printers, speakers, vibration systems, and direct write of computer-readable instructions to memory devices and mechanisms. Such memory devices and mechanisms can include by way of example and not limitation, removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer. In addition to the bus system 16010, examples of interfaces through which the output device 16150 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein some of the computing components can be located remotely and connected to via a wired or wireless network. By way of example and not limitation, The Computing Environment FIG shows a cloud 16210 and a remote data source 16240 connected to the main system bus 16010 via bus routes 16220 and 16230 respectively. The cloud computing infrastructure 16210 can itself contain any number of computing components or a complete computing environment in the form of a virtual machine (VM). The remote data source 16240 can be connected via a network to any number of external sources such as NMR spectrometry devices, X-ray diffraction devices, electron microscopes, imaging devices, imaging systems, or imaging software.

In some embodiment of the invention disclosed herein, a sensor system 16060 which captures and pre-processes data is attached directly to the system. For example, this may be an electron microscope (and associated image processing software); it may be a camera in the case of an imaging system, say for processing distance map photographs; or it may be an X-ray crystallography machine or an NMR spectrometer (and associated software), excetera. Stored in the memory mechanism—16020, 16240, or 16210—are machine learning models, algorithms, and data products developed according to the procedures set-forth herein. Computer-readable instructions are also stored in the memory mechanism, so that upon command, protein structure representation data, its substrates and associated data can be captured or can be received over a network from a remote or local previously collated database. This transmission of data can be done over a wired or wireless network as previously detailed, as the source and/or recipient of the data output can be at a remote location.

The objects set forth in the preceding are presented in an illustrative manner for reason of efficiency. It is hereby noted that the above disclosed methods and systems can be implemented in manners such that modifications are made to the particular illustration presented above, while yet the spirit and scope of the invention is retained. The interpretation of the above disclosure is to contain such modifications, and is not to be limited to the particular illustrative examples and associated drawings set-forth herein.

Furthermore, by intention, the following claims encompass all of the general and specific attributes of the invention described herein; and encompass all possible expressions of the scope of the invention, which can be interpreted—as pertaining to language—as falling between the aforementioned general and specific ends.

What is claimed:

1. A method, comprising:
   a) receiving, at a processor, representations of a plurality of proteins:
      i) wherein for each of the plurality of proteins, the representations include a representation of the protein's sequence and structure,
      ii) wherein for each of the plurality of proteins, the representations include a representation of one or more specified conditions on the protein;
   b) using the representations of the plurality of proteins to train a neural network:
      i) wherein the neural network is configured to accept a representation of one or more specified conditions as input, and wherein the training objective is to yield as output, a representation of a protein associated with the one or more specified conditions,
      ii) wherein the neural network has at least two heads, including a sequence head which generates the output protein's sequence and a structure head which generates the output protein's structure,
      iii) wherein during training, there is a loss function computation corresponding to the sequence head output and a different loss function computation corresponding to the structure head output, and wherein backpropagation and weight updates proceed backwards independently from each of the heads through the ancestral nodes of the respective head,
      iv) wherein some non-head weights of the neural network are shared,
      v) wherein the neural network is a transformer:
   c) using the trained neural network to generate a protein representation, given a representation of the specified condition(s) as input:
      i) wherein a sequence and structure representation of the generated protein is returned as output.

2. The method of claim 1, wherein the output protein is synthesized.

3. The method of claim 1, wherein the sequence head's final output is a probability distribution over amino acids and auxiliary tokens; and wherein the structure head's final output is a probability distribution over possible structure parameters associated with each residue.

4. The method of claim 3, wherein the sequence and structure generation is via an autoregressive procedure.

5. The method of claim 4, wherein the specified condition is a target receptor and the specified condition's representation is a representation of the target receptor's sequence and structure; and wherein the output protein is a peptide ligand drug.

6. The method of claim 5, for generating a representation of a peptide ligand drug's sequence and structure given a representation of a target receptor's sequence and structure, wherein the method is also for obtaining and synthesizing an effective peptide ligand drug, the method further comprising:
   a) using the trained transformer to obtain a representation of a peptide ligand drug, given a representation of a target receptor;
      i) wherein, during autoregression, each residue is determined by randomly sampling the output probability distribution of the sequence head,
      ii) wherein, during autoregression, the structure parameters associated with each residue are determined by randomly sampling the output probability distribution of the structure head,
   b) repeating the random sampling-based peptide ligand drug representation generation procedure a plurality of times, thereby generating a plurality of representations of candidate peptide ligand drugs;
   c) assessing the binding interaction and efficacy of each of the generated candidate peptide ligand drug representations;
   d) selecting the most effective candidate peptide ligand drug;
   e) synthesizing the peptide ligand drug.

7. The method of claim 4, wherein the specified condition is a peptide antigen and the specified condition's representation is a representation of the peptide antigen's sequence and structure; and wherein the output protein is an associated antibody.

8. The method of claim 7, for generating a representation of an antibody given a peptide antigen, wherein the method is also for obtaining and synthesizing an effective antibody for a given peptide antigen, the method further comprising:

a) using the trained transformer to generate an antibody:
   i) wherein for each residue position, the output probability distribution of the sequence head is randomly sampled to determine the amino acid residue,
   ii) wherein for each residue position, the output probability distribution of the structure head is randomly sampled to determine the associated structure parameters;
b) repeating the sampling-based antibody generation procedure a plurality of times, each yielding an antibody's representation;
c) assessing the representation of each of the plurality of antibodies for antigen binding specificity, fc region properties, and efficacy;
d) selecting the most effective represented antibody based on the assessment;
e) synthesizing the antibody.

9. The method of claim 8, wherein the antigen is a component or product of a pathogen, and wherein the antibody is a monoclonal antibody (mAb) drug.

10. The method of claim 8, wherein the antigen is an endogenous protein and the antibody is a synthetic biologic drug.

11. The method of claim 4, wherein the specified conditions are a set of desired properties of the output protein; wherein the possible values of each property are categorical classes, each numerically encoded:
   a) wherein the specified conditions are represented by a vector of length equal to the number of properties, as each entry position holds the value of the respective specified property;
   b) wherein each specified property is numerically encoded categorically or continuously.

12. The method of claim 11, wherein the output protein is a peptide ligand for a given target protein.

13. The method of claim 12, wherein the given target protein is a receptor, and wherein the peptide ligand represented by the output is synthesized.

* * * * *